United States Patent
Golovlev et al.

(10) Patent No.: US 8,206,905 B2
(45) Date of Patent: Jun. 26, 2012

(54) ENZYMATIC TIME-RESOLVED LUMINESCENT ASSAY FOR NUCLEIC ACIDS QUANTITATION

(76) Inventors: Valeri Golovlev, Oak Ridge, TN (US); Ye Sun, Knoxville, TN (US)

( * ) Notice: Subject to any disclaimer, the term of this patent is extended or adjusted under 35 U.S.C. 154(b) by 750 days.

(21) Appl. No.: 12/110,297

(22) Filed: Apr. 26, 2008

(65) Prior Publication Data

US 2009/0317803 A1    Dec. 24, 2009

(51) Int. Cl.
*C12Q 1/68*    (2006.01)
(52) U.S. Cl. ........................................ 435/6.1
(58) Field of Classification Search .................. None
See application file for complete search history.

(56) References Cited

U.S. PATENT DOCUMENTS

| | | | |
|---|---|---|---|
| 6,210,891 | B1 | 4/2001 | Nyren et al. |
| 6,258,568 | B1 | 7/2001 | Nyren |
| 6,270,973 | B1 | 8/2001 | Lewis et al. |
| 6,828,100 | B1 | 12/2004 | Ronaghi |
| 7,141,370 | B2 | 11/2006 | Hassibi et al. |
| 2004/0197793 | A1* | 10/2004 | Hassibi et al. ............ 435/6 |
| 2004/0248227 | A1 | 12/2004 | Jansson et al. |

OTHER PUBLICATIONS

F. Sanger, S. Nicklen, and A.R. Coulson, "DNA sequencing with chain-terminating inhibitors ",Proc. Natl. Acad. Sci., 74(12):5463-7, 1977.
P. Nyrén, A. Lundin , "Enzymatic method for continuous monitoring of inorganic pyrophosphate synthesis", Anal Biochem. 151(2):504-9, 1985.
P. Nyren, "Enzymatic Method for continious monitoring of DNA polymerase activity", Anal. Biochem., 167:235-238, 1987.
L.G. Birkenmeyer, I.K. Mushahwar,"DNA probe amplification methods", J Virol Methods. Nov.-Dec. 35 (2):117-26, 1991.
U. Landegren, "Molecular mechanics of nucleic acid sequence amplification", Trends Genet. 9(6):199-204, 1993.
Y. Nishinaka, Y. Aramaki, H. Yoshida, H. Masuya, T. Sugawara, Y. Ichimori , "A new sensitive chemiluminescence probe, L-012, for measuring the production of superoxide anion by cells", Biochem Biophys Res Commun 193(2):554-559, 1993.
M. Nilsson, H. Malmgren, M. Samiotaki, M. Kwiatkowski, B.P. Chowdhary, U. Landegren, "Padlock Probes: Circularizing Oligonucleotides for Localized DNA Detection", Science, 265: 2085-2088, 1994.
A. Fire, S.Q. Xu, "Rolling replication of short DNA circles", Proc Natl Acad Sci U S A. 92(10):4641-5, 1995.
M. Ronaghi, S. Karamohamed, B. Pettersson, M. Uhlén, P. Nyrén, "Real-time DNA sequencing using detection of pyrophosphate release", Anal Biochem. 242(1):84-9, 1996.
P. Nyrén, S. Karamohamed, M. Ronaghi., "Detection of single-base changes using a bioluminometric primer extension assay.", Anal Biochem. 15;244(2):367-73, 1997.
B. Schweitzer, S. Wiltshire, J. Lambert, S. O'Malley, K. Kukanskis, Z. Zhu, S.F. Kingsmore, P.M. Lizardi, D.C. Ward, "Inaugural article: immunoassays with rolling circle DNA amplification: a versatile platform for ultrasensitive antigen detection", Proc Natl Acad Sci U S A. Aug. 29;97(18):10113-9, 2000.
M. Ronaghi, "Pyrosequencing sheds light on DNA sequencing", Genome Res. Jan. 2001 11(1):3-11, 2001.
A. Hassibi, C. Contag, M.O. Vlad, M. Hafezi, T.H. Lee, R.W. Davis,. N. Pourmad, "Bioluminescence regenerative cycle (BCR) system:Theoretical consideration for nucleic acid quantification assays", Biophys. Chemistry, 116:175-185, 2005.
Y. Sun and V. Golovlev, "Bioluminescent assay for RNA quantitation", Luminescence 21:293, 2006.

* cited by examiner

*Primary Examiner* — Christopher M. Babic

(57) ABSTRACT

The objects of the present invention are to provide a new technology platform for quantitation number of copies of nucleic acid molecules of interest by lumonogenic (i.e., enzymatic luminescence) detection. The detection approach of the method of present invention is essentially employing time-resolved approach, e.g., based on detection transient parameters of luminescent signal. The various disclosed embodiments allow DNA and RNA quantification in a broad dynamic range; can be used for detection of DNA, as well as long (mRNA) and short (microRNA) RNA targets. The present invention provides methods, instruments, and kits for fast and highly sensitive identification and measurements of nucleic acids in various life science and biomedical applications.

4 Claims, 12 Drawing Sheets

$$PPi + APS \xrightleftharpoons{ATP-Sulfurylase} ATP + SO_4^{-2}$$

$$ATP + luciferin + O_2 \xrightarrow{Luciferase} AMP + oxyluciferin + CO_2 + h\upsilon + PPi$$

FIG.4

AMP + Phosphoenolpyruvate + PPi $\xrightarrow{\text{pyruvate, orthophosphate dikinase}}$ ATP + Pyruvate + Pi $ATP + luciferin + O_2 \xrightarrow{Luciferase} AMP + oxyluciferin + CO_2 + h\upsilon + PPi$

FIG.5

1) IMP + PPi → *phosphoribosyl pyrophosphate* + hypoxanthine 2) hypoxanthine + $H_2O$ + $O_2$ → xanthine + $H_2O_2$ 3) xanthine + $H_2O$ + $O_2$ → urate + $H_2O_2$ 4) urate + $2H_2O$ + $O_2$ → allantoin + $CO_2$ + $H_2O_2$ 5) luminol + $H_2O_2$ → 3-APA + $N_2$ + hv.

FIG.6

ENZYMATIC TIME-RESOLVED LUMINESCENT ASSAY FOR NUCLEIC ACIDS QUANTITATION

The present application claims priority to U.S. Provisional Application Ser. No. 60/912,924 filed on Apr. 27, 2007.

REFERENCE TO SEQUENCE LISTING AND INCORPORATION BY REFERENCE THEREOF

The present application includes a Sequence Listing in electronic format, filed at the time of submitting application on Apr. 26, 2008.

BACKGROUND OF THE INVENTION

1. Filed of Invention

The present invention relates to the field of molecular biology. More specifically, the invention relates to methods, compositions, kits and apparatus for detection, identification and quantification of biomolecules. In certain embodiments of the invention, the biomolecules may be a nucleoside, nucleotide, oligonucleotide, polynucleotide, nucleic acid and other biological agents known to those skilled in the art. In particular embodiments of the invention, the methods involve use of enzymatic luminescence reaction and optical detection for quantitation the number of target molecule in biological samples.

2. Description of Related Art

Recognition and quantitation of level of DNA and RNA (gene expression) in biological samples is required in many fields of life science research, drug discovery, clinical diagnosis, and environmental analysis. While microarrays emerged as a dominant tool for large-scale DNA analysis and gene expression research, the alternative non-array gene expression technologies can be superior to microarrays in accuracy and sensitivity. Non-array techniques include quantitative Polymerase Chain Reaction (RT-qPCR), Serial Analysis of Gene Expression (SAGE), Northern blots, differential display, and Massively Parallel Signature Sequencing (MPSS). Now considering quantitation of gene expression as example, it is appreciated that some embodiments of this invention can be applied for recognition and quantitation of biomolecules including a nucleoside, nucleotide, oligonucleotide, polynucleotide, nucleic acid, peptide, polypeptide, protein, carbohydrate, polysaccharide, glycoprotein, lipid, hormone, growth factor, cytokine, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, and other biological agents known to one skilled in the art.

Microarrays have been increasingly applied as a multiplexed tool for monitoring expression levels of thousands of genes in samples under various conditions. Microarrays have been undeniably successful in many applications. Yet, data quality is a major concern of microarray-based studies. It is clear that the validation of results from microarray experiments by other methods is essential. Indeed, multiple factors can contribute to the errors, including variations in microarray manufacturing, cDNA generation and labeling, hybridization, and instrumental errors during image acquisition and quantification. Quantitative RT-qPCR and Northern blot are two most commonly used follow-up techniques for validation of microarray results, as these techniques have higher sensitivity and accuracy.

The real time quantitative PCR (RT-qPCR) is often considered to be the gold standard and the method of choice for mRNA quantification. The method utilizes a pair of synthetic oligonucleotides, or primers, each hybridizing to unique sites on the two strands of a double-stranded DNA (dsDNA) target, with the pair spanning a region that will be exponentially reproduced. The hybridized primers act as substrates for DNA polymerase, which create a complementary strand via sequential addition of deoxynucleotides to hybridized primers. An intercalating fluorogenic agent (SYBR green) or dye/quencher reporter probes are employed for monitoring the progression of PCR amplification. The amount of target RNA is measured by determining the number of amplification cycles, $C_t$, required to produce amount of PCR products that exceed a certain threshold level of detection.

Several factors have contributed to the transformation of RT-qPCR technology into a mainstream research tool: (i) as a homogeneous assay it avoids the need for post-PCR processing; (ii) a wide ($>10^7$-fold) dynamic range allows straightforward comparison between RNAs that differ widely in their abundance; and (iii) the assay realizes the inherent quantitative potential of the PCR, as well as its qualitative uses.

Yet, RT-qPCR is not pitfall-free. Some of the problems have their roots in quantitative nature of this technology and may result from the close association between quantification and amplification efficiency. Often the nature and extent of the unreliability of quantitative RT-PCR data is still not widely appreciated or acknowledged. One example is the threshold cycle $C_t$, which records the cycle when sample fluorescence exceeds a chosen threshold of the background fluorescence. The $C_t$ is used for quantifying target copy number, yet its value is subjective and can be altered at will making it difficult to compare results from different platforms and at various experimental conditions. Another important issue is the reverse transcription step of RT-qPCR process. What is often pursued as a simple and small step of converting RNA into a cDNA template is an important contributor to the variability and lack of reproducibility frequently observed in RT-qPCR experiments. This is especially the case when cDNA priming in real-time RT-qPCR assays is carried out using random primers or oligo(T). The random primers create problems if the mRNA targets are varied in size significantly since a single mRNA specie can be represented by multiple transcripts and the number of representing transcripts is proportional to mRNA length. It has been demonstrated that random hexamers can overestimate mRNA copy numbers by more than order of magnitude compared with a sequence-specific primer. The oligo(T)s bind to the poly(A) tail and require full-length RNA, which are not an effective choice for transcribing RNA that is likely to be fragmented by partial degradation. Also, the oligo(T) primed reactions usually have significantly lower linear range for reverse transcription and may distort the accurate determination of target abundance.

Recently an alternative approach for quantitation of nucleic acids has been introduced, in which two or more enzymatic reaction produce pyrophosphate (PPi) and generate a detectable luminescence signal (Nyren and Lundin, Anal. Biochem. 1512:504-9.1985; Nyren, Anal. Biochem. 167:235-238, 1987, incorporated herein by reference). The approach is based on detection of released inorganic pyrophosphate during oligonucleotide synthesis by polymerase extension reaction (PCR) as illustrated in Drawing 1. The target nucleic acid molecule can be either RNA or DNA. In series of three consecutive enzymatic reactions the released PPi is converted into ATP by ATP-sulfurylase, and subsequently, the ATP provides the energy to luciferase to oxidize luciferin and generate light. The PPi identification technique is extremely sensitive and potentially can detect a single target DNA or RNA molecule. This is possible because the synthesis of a single large cDNA can require incorporation of thousands of deoxynucleotides, consequently producing thousands of ATP molecules by respective enzymatic reactions and resulting in emission from hundreds to thousands of photons per each cDNA copy synthesized.

Furthermore, for increasing detection sensitivity a bioluminescent regenerative cycle assay system has been recently introduced (Hassibi et al, U.S. Pat. No. 7,141,370, incorporated herein by reference). The regenerative cycle uses the ATP-sulfurylase enzyme (E.C. 2.7.7.4) to convert PPi to ATP. In the presence of luciferin and luciferase the consumption of the ATP molecule results in light emission and formation of a PPi molecule as a by-product. This by-product PPi molecule can be re-used in another cycle of ATP production and subsequent light emission. The advantage of the regenerative bioluminescence system is that each PPi molecule can initiate potentially unlimited number of light emission cycles, producing steady-state emission with the intensity proportional to the number of PPi molecules in sample. Yet, the regenerative system has a serious drawback. The real biological samples unavoidably carry some residual amount of ATP molecules (ATP contamination), that alone with target PPi molecules can be involved as a substrate in the regenerative cycle. In addition, the biological samples exhibit steady-state luminescence (luminescence background), which is originated by non-ATP substrate(s) in samples. The ATP contamination and steady-state luminescence background reduces the sensitivity and distorts the accuracy of PPi measurement by the regenerative cycle assay.

In view of the existing drawbacks the known in the art PPi detection techniques are suitable mostly for qualitative detection in applications such as pyrosequencing, i.e., for determination of DNA sequence (Ronaghi et al., Anal. Biochem. 242:84-89, 1996) and SNP detection (Nyren et al., Anal. Biochem. 244:367-373, 1997, all references herein incorporated by reference in its entirety). Indeed, set alone the interference from contamination and background luminescence, under the existing techniques the bioluminescent signal is proportional to the number of incorporated nucleotides rather than to the number of target molecules. A small number of long oligonucleotide targets can produce comparable luminescence signal as a large number of short oligonucleotides. This drawback makes it difficult or even impossible to measure the number of DNA copies based on the intensity of the bioluminescent signal alone. The same is applicable to the detection of RNA by RNA reverse transcription reaction and bioluminescence detection: the longer RNA sequence is, the more deoxynucleotides are incorporated into cDNA by transcriptase, and the higher the intensity of luminescent signal is detected independently of the actual number of target RNA molecules in sample substance.

Therefore, there are sources of error in PPi detection methods, such as where targets structural differences lead to different efficiencies; or, for example, different replication events are involved for different target sequences; or differences in the rates of probe-target hybridization may exist for different targets thus resulting in varying rates of replications; or random termination of replication reaction; due to the possibility that small differences in replication rate due to non-homogeneous reaction condition result in undesirably large differences in the rate of PPi release when long target molecules are replicated. Therefore, the known in the art methods of enzymatic luminescent detection of nucleic acids in its present state often are not suitable for applications required accurate measurements of the number of copies of target molecules.

While a large number of detection methods for use with nucleic acids and protein arrays have been described in patents and in the scientific literature, virtually all methods set forth in prior art contain one or more inherent weaknesses. Some lack the sensitivity necessary to accomplish certain tasks. Other methods lack the recognition specificity or produce response, which resulted both from the size and the number of target molecules rather than to represent the number of copies of said target molecules. Yet, some methods have drawbacks due to interference from contaminants present in sample. Still others are expensive and difficult to implement or present health safety concerns for workers, who implement these techniques.

Thus, there is a need for an improved method and kit for luminogenic recognition and quantitation of nucleic acid molecules, which said method is quantitative, sensitive, does not required chemical modification of the target molecules for detection and which said method is simple to implement and is able to address drawbacks of the existing techniques. Furthermore, there is a need for providing method, instrumentations, and kits for quantitative comparison of the number of different species of nucleic acid molecules in presence of contaminants producing background luminescence, said method producing luminescent signal proportional to the number of target molecules even if the sequence length of target nucleic acid molecules is varied substantially across different species or even the same specie.

Nomenclature

Unless defined otherwise, all technical and scientific terms used above and throughout the text have the same meaning as commonly understood to one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents and other references are incorporated in to herein by reference. In addition, the materials, methods, and examples are illustrative only and not intended to be limiting.

Terms that are not otherwise defined herein are used in accordance with their plain, ordinary meaning.

The following definitions are provided to facilitate a clear understanding of the present invention. The term "analyte", "target", "target molecule" or "molecular target" refers to a macro-molecule, without limitation as to size, including a nucleoside, nucleotide, oligonucleotide, polynucleotide, nucleic acid, nucleic acid single-stranded or double-stranded polymer and equivalents thereof known in the art, peptide, polypeptide, protein, carbohydrate, polysaccharide, glycoprotein, lipid, hormone, growth factor, cytokine, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, and other biological agents known to those skilled in the art. "Targets" are not limited to single molecules or atoms, but may also comprise complex aggregates, such as a virus, bacterium, *Salmonella, Streptococcus, Legionella, E. coli, Giardia, Cryptosporidium, Rickettsia*, spore, mold, yeast, algae, amoebae, dinoflagellate, unicellular organism, pathogen or cell. In certain embodiments, cells exhibiting a particular characteristic or disease state, such as a cancer cell, may be targets. Virtually any chemical or biological compound, molecule or aggregate could be a target, so long as it can be attached to a nucleic acid, polynucleotide or oligonucleotide molecule by any type of intermolecular interaction.

The term "nucleic acid" means either DNA, RNA, single-stranded, double-stranded or triple stranded and any chemical modifications thereof. Virtually any modification of the nucleic acid is contemplated by this invention. "Nucleic acid" encompasses, but is not limited to, oligonucleotides and polynucleotides. Within the practice of the present invention, a "nucleic acid" may be of any length.

"Protein" is used herein to refer to any polymer comprised of amino acids, chemically modified amino acids, amino acid analogues and/or amino acid derivatives. The term "protein" encompasses amino acid polymers of any length, from two amino acid residues up to a full length protein. As used herein, the term "protein" encompasses, but is not limited to, peptides, oligopeptides and polypeptides.

The term "bound molecules", "duplex" or "hybridized molecules" refers to a corresponding pair of molecules held together due to mutual affinity or binding capacity, typically specific or non-specific binding or interaction, including biochemical, physiological, and/or pharmaceutical interactions. Herein binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "sample substance" refers to a media, often a liquid media, which was prepared for the purpose of analysis and establishing (a) the presence or absence of a particular type of molecular target; (b) the presence or absence of a plurality of molecular targets; (c) the presence or absence of specific groups of molecular targets; (d) and if the target molecules are present, to determine/quantify the number of target molecules present in the sample substance.

The term "probe molecular structure" or "probe" refers to a molecule of known nature, which said molecule is capable of binding to a particular type of target molecule or to any biological or chemical agent of interest, or to plurality of target molecules from a specific class/group of molecules. Said probe is used to witness the presence of the corresponding target molecule or a specific class of target molecules in a sample substance.

The abbreviation "DNA/RNA" means "DNA, or equally acceptable, RNA".

The term "enzymatic luminescence" refers to one or more consecutive biochemical reactions involving at least one reaction of enzyme(s) and substrate(s) which said consecutive reactions are producing light as result of chemical or biochemical modification of the molecules involved.

The term "replication reaction" and "replication of nucleic acid" refers to a enzymatic biochemical reaction involving primer and template, in which reaction the primer and template have a homology and shorter primer molecules is extended according to the sequence of the longer template molecules. Examples of replication reaction include, but not limited to, the polymerase chain reaction (PCR), ligase chain reaction (LCR), self-sustained sequence replication (3SR), nucleic acid sequence based amplification (NASBA), strand displacement amplification (SDA), amplification with Qβ replicase (Birkenmeyer and Mushahwar, J. Virological Methods, 35: 117-126 (1991); Landegren, Trends Genetics, 9: 199-202 (1993)) as well as "constant temperature" PCR and rolling circle amplification (Fire A., Xu S. Q, PNAS 92:4641-4645 (1995)), the contents each of which are incorporated herein by reference.

The terms polymerase and reverse transcriptase refers to enzymes known in the art for carrying DNA and RNA replication reactions. Non-limiting examples include DNA polymerases, reverse transcriptases, and RNA-dependent RNA polymerases. Non-limiting examples of polymerases that may be of use include *Thermatoga maritima* DNA polymerase, AmplitaqFS™ DNA polymerase, Taquenase™ DNA polymerase, ThermoSequenase™, Taq DNA polymerase, Qbeta™ replicase, T4 DNA polymerase, *Thermus themophilus* DNA polymerase, RNA-dependent RNA polymerase and SP6 RNA polymerase. Commercially available polymerases including Pwo DNA Polymerase from Boehringer Mannheim Biochemicals (Indianapolis, Ind.); Bst Polymerase from Bio-Rad Laboratories (Hercules, Calif.); IsoTherm™ DNA Polymerase from Epicentre Technologies (Madison, Wis.); Moloney Murine Leukemia Virus Reverse Transcriptase, Pfu DNA Polymerase, Avian Myeloblastosis Virus Reverse Transcriptase, *Thermus flavus* (Tfl) DNA Polymerase and *Thermococcus litoralis* (Tli) DNA Polymerase from Promega (Madison, Wis.); RAV2 Reverse Transcriptase, HIV-1 Reverse Transcriptase, T7 RNA Polymerase, T3 RNA Polymerase, SP6 RNA Polymerase, RNA Polymerase *E. coli, Thermus aquaticus* DNA Polymerase, T7 DNA Polymerase +/−3'.fwdarw.5' exonuclease, Klenow Fragment of DNA Polymerase I, *Thermus 'ubiquitous'* DNA Polymerase, and DNA polymerase I from Amersham Pharmacia Biotech (Piscataway, N.J.), Method of using polymerases and compositions suitable for use in various methods are well known in the art (e.g., U.S. Pat. No. 7,141,370) and incorporated herein by reference in its entirety.

The abbreviation ATP refers to adenosine-5'-triphosphate, CAS No. 56-65-5.

The abbreviation PPi refers to inorganic pyrophosphate, CAS No. 13472-36-1.

The abbreviation APS refers to adenosine 5'-phosphosulfate, CAS No. 485-84-7.

The abbreviation PCR refers to Polymerase Chain Reaction, which is technique for amplifying quantity of DNA, see, e.g., U.S. Pat. Nos. 5,656,493; 5,234,824; and 5,187,083, the contents each of which are incorporated herein by reference.

The abbreviation RT-qBLA refers to real time quantitative PCR method known in the art for detection and quantitation of nucleic acids.

It must be noted that as used herein and in the appended claims, the singular forms "a", "and", and "the" include plural referents unless the context clearly dictates otherwise. Thus, for example, reference to "a target molecule" may include a plurality of macro-molecules, including organic compounds, antibodies, antigens, virus particles, metals, metal complexes, ions, cellular metabolites, enzyme inhibitors, receptor ligands, nerve agents, peptides, proteins, fatty acids, steroids, hormones, narcotic agents, synthetic molecules, medications, nucleic acid single-stranded or double-stranded polymers and equivalents thereof known to those skilled in the art, and so forth.

SUMMARY OF THE INVENTION

The objects of the present invention are to provide a new technology platform for quantitation number of copies of nucleic acid molecules of interest by lumonogenic (i.e., enzymatic luminescence) detection. The detection approach of the method of present invention is essentially employing time-resolved approach, e.g., based on detection transient parameters of luminescent signal as opposed to measurement of steady-state luminescence parameters known in the art (U.S. Pat. No. 7,141,370 incorporated herein by reference in its entirety)

The present invention is directed to a methods, instruments, and kits for fast and highly sensitive identification and measurements of nucleic acids in various life science and biomedical applications. The various disclosed approaches allow DNA and RNA quantification in a broad dynamic range; can be used for detection of DNA, as well as long (mRNA) and short (microRNA) RNA targets; the provided methods require less reagents per reaction that other techniques known in the art; normally is performed at a constant temperature and is amendable to various replication strategies including "constant temperature" PCR and rolling circle amplification; the methods of present invention can be implemented using equipment, which costs a fraction of the real time RT-qPCR systems.

Now, specific examples of the method of present invention are provided herein below by way of illustration and not by way of limitation. An ordinary skilled artisan will recognize many various ways of practicing the method of present invention.

BRIEF DESCRIPTION OF DRAWINGS

FIG. 4: In various embodiments of the method of present invention, the enzymatic luminescence detection of pyrophosphate can be carried out by converting PPi into ATP by ATP-Sulfurylase followed by luciferin/luciferase bioluminescence reaction.

FIG. 5: Yet, in another embodiment, conversion of PPi to ATP can be carried out by pyrivate orthophosphate phosphotransferase (EC 2.7.9.1) followed by luciferin/luciferase ATP detection.

FIG. 6: Considering embodiment in which PPi molecules detected by chemiluminescence detection, the reaction most preferably is performed according to set of consecutive enzymatic reactions comprises: a) reacting inorganic pyrophosphate present in a sample with inosine 5'-monophosphate or xanthosine 5'-monophosphate in the presence of hypoxanthine phosphoribosyltransferase (E.C. 2.4.2.8) or xanthine phosphoribosyltransferase (E.C. 2.4.2.22), and xanthine oxidase (E.C. 1.1.3.22) and determining production of hydrogen peroxide as a measure of inorganic pyrophosphate in the sample.

DESCRIPTION OF ILLUSTRATIVE EMBODIMENTS

Figure 1:
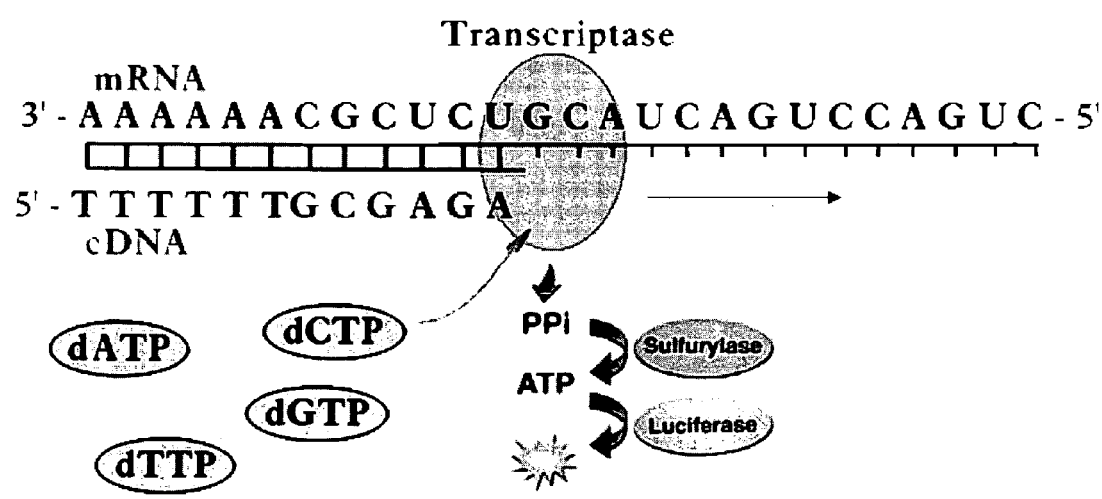
FIG. 1: Detection concept of the method of present invention for detection nucleic acid target molecules. Here, pyrophosphate is generated by specific replication of target nucleic acid molecule by polymerase or reverse transcriptase reaction. The pyrophosphate molecules are converted by a set of consecutive enzymatic reactions and luminescent photons are emitted.
Figure 2:
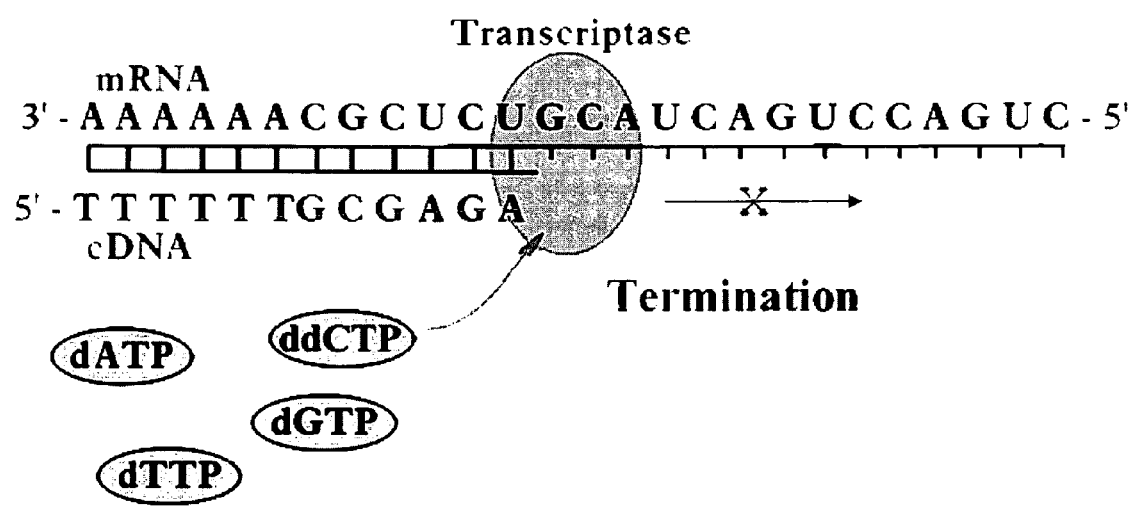
FIG. 2: Illustration of the approach for terminating replication reaction by incorporating dideoxynucleotide into sequence of cDNA copy. Termination of the replication reaction subsequently terminate generation of pyrophosphate molecules.
Figure 3:
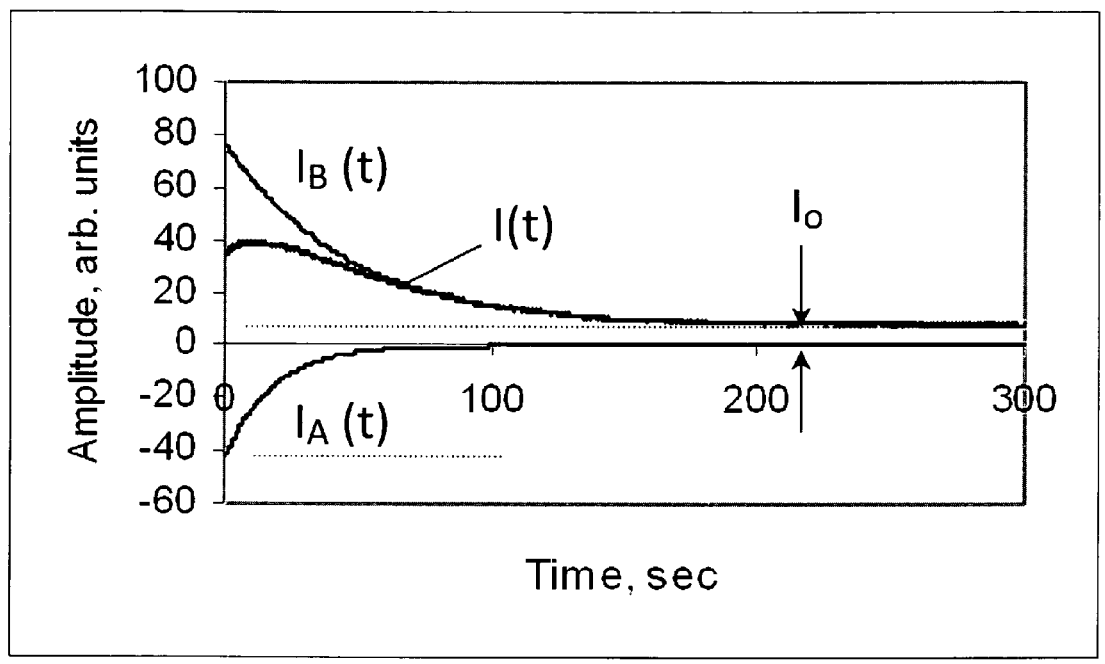
FIG. 3: In various embodiments of the invention, a set of enzymes and reagents for detection pyrophosphate is formulated to allow measurement of three components of the luminescence: the pyrophosphate component $I_A(t)$, the ATP component $I_B(t)$, and steady-state background component, $I_o$, of the luminescent signal, which is given by $I(t)=I_A(t)+I_B(t)+I_o$
Figure 7:
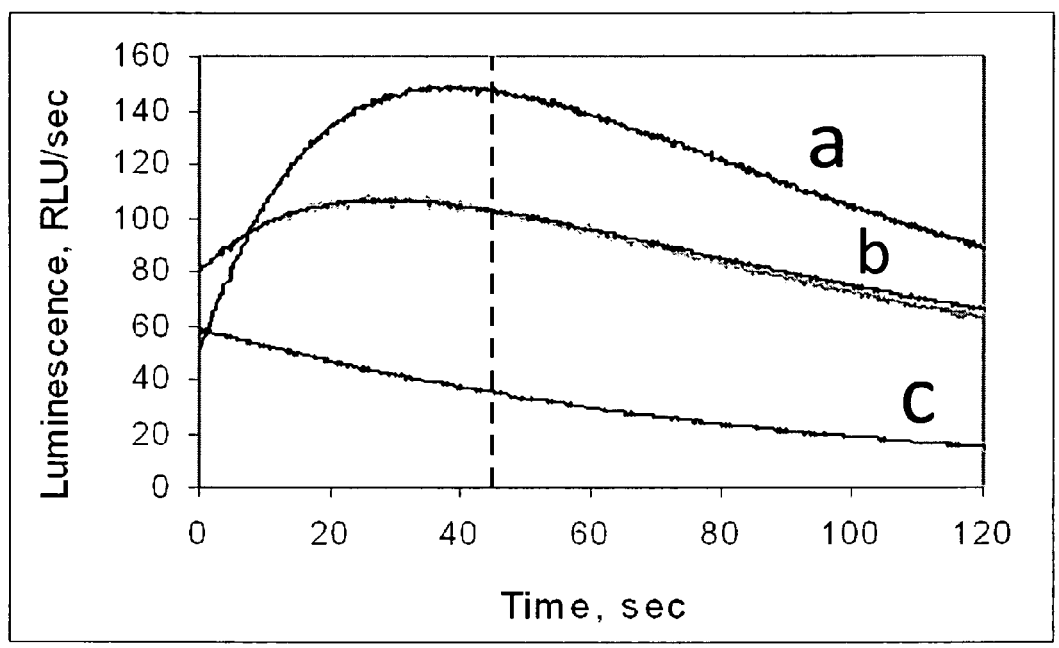
FIG. 7: Detection of PPi in sample contaminated with ATP: (a) 10 pg of PPi and no ATP in sample; (b) 5 pg PPi and 1 pg of ATP; (c) No PPi and 1 pg of ATP.
Figure 8:
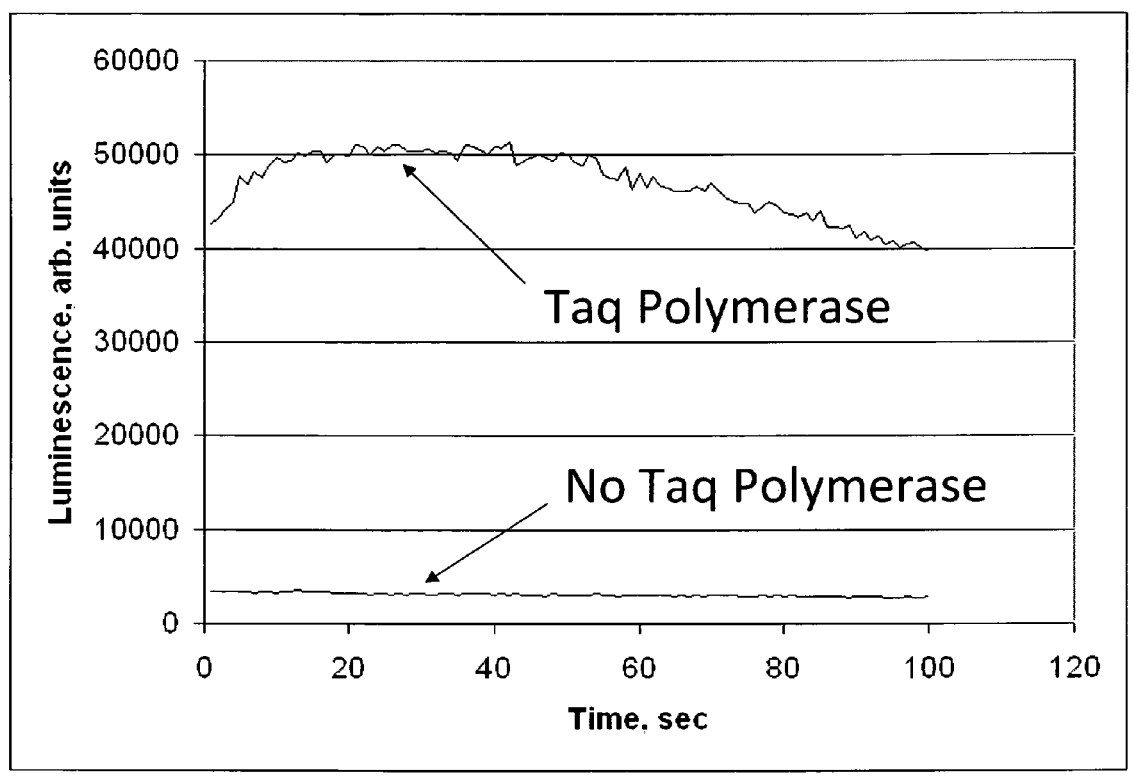
FIG. 8: Detection of DNA M13mp18 replication by Taq DNA polymerase synthesis reaction: shown here is detection of release of pyrophosphate by polymerase reaction in real time (Taq polymerase added) vs. luminescent signal from negative control sample with no Taq polymerase added.
Figure 9:
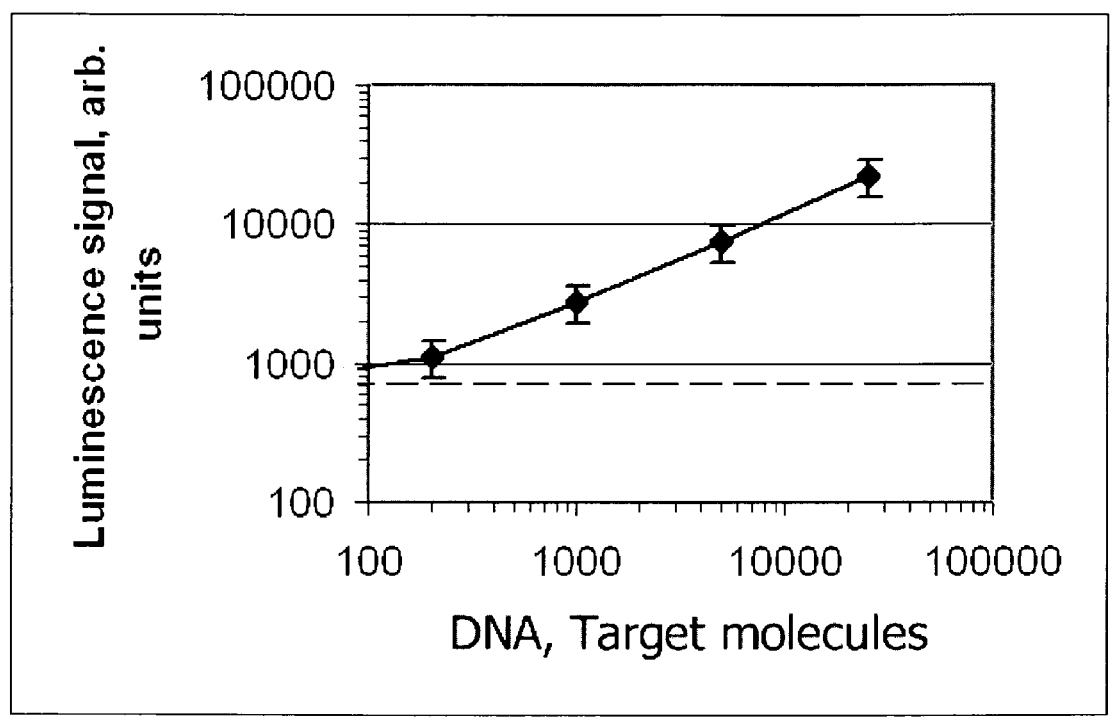
FIG. 9: Standard curve illustrate detection sensitivity of the method of present invention for detection M13mp18 phage DNA replicated by Tad DNA polymerase in presence of sequence-specific primer.
Figure 10:
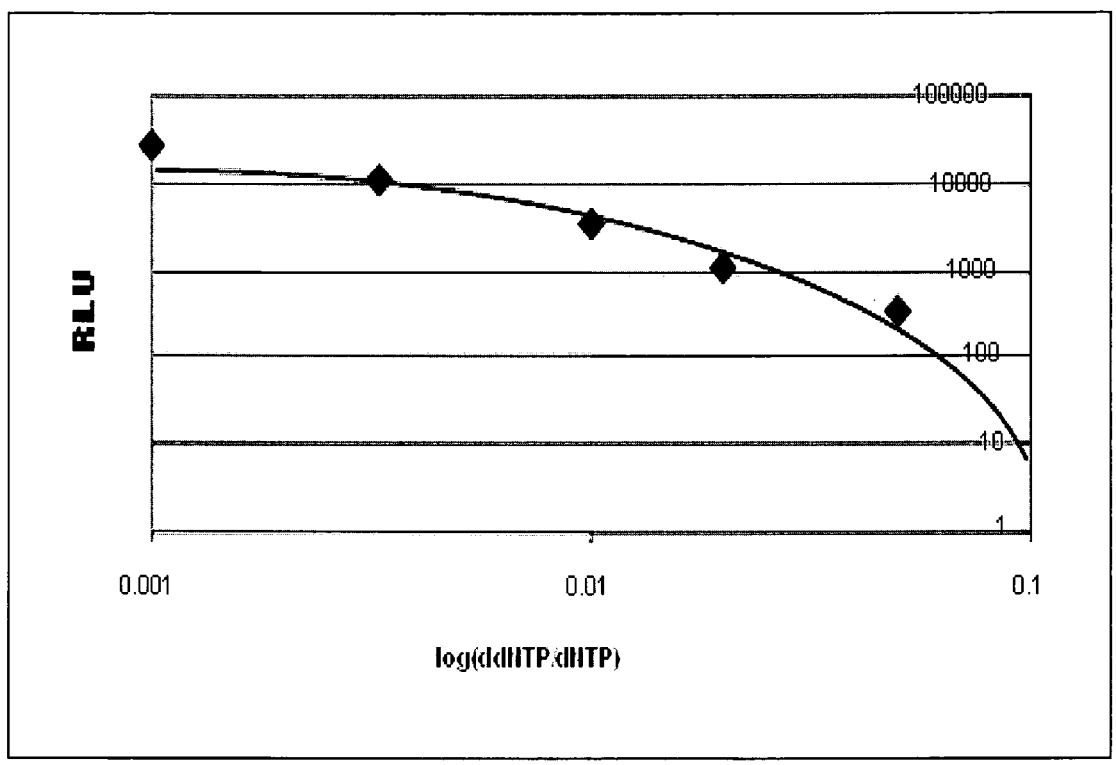
FIG. 10: Programmable termination of a replication reaction in this example is demonstrated by detecting M13mp18 DNA replication in reaction solutions containing ddNTP:dNTP at the ratio of 1:20, 1:50, 1:100, 1:300 and 1:1000. Increasing the concentration of ddNTP reduces the intensity of luminescent signal due to termination of pyrophosphate synthesis after ddNTP incorporation into cDNA sequence.
Figure 11:
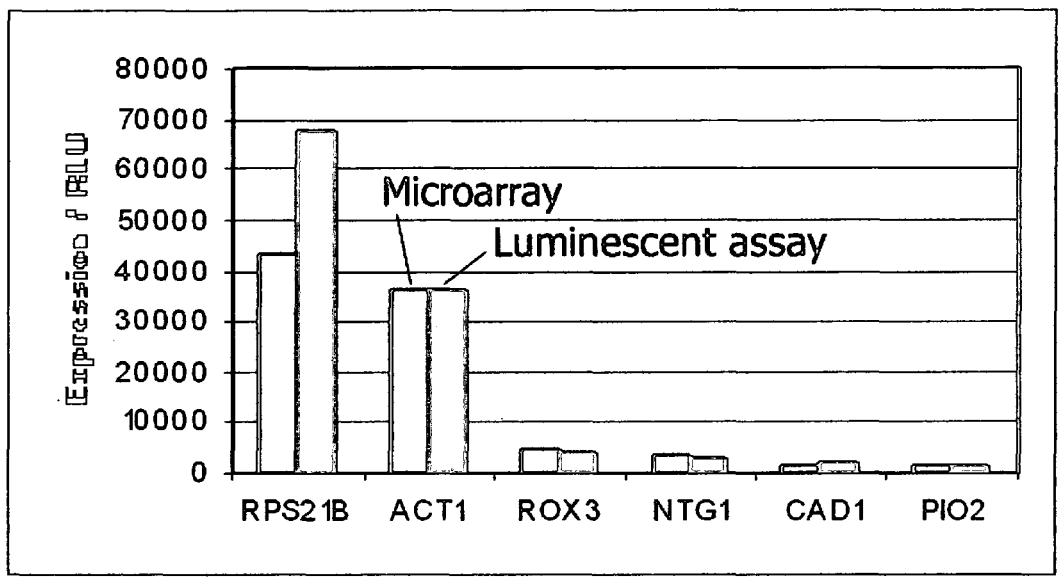
FIG. 11: Comparison of expression value of six genes detected in total yeast RNA sample by bioluminescent assay of the method of present invention and by Affymetrix S98 yeast array.
Figure 12:
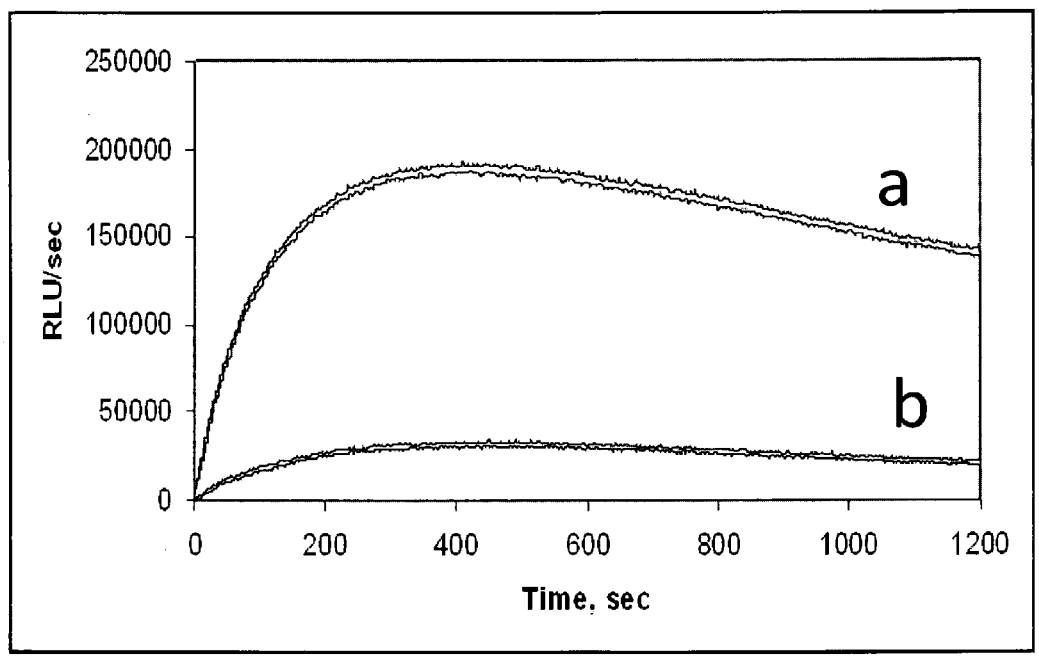
FIG. 12: Activity of HIV-1 reverse transcriptase (a) in absence of HIV-1 inhibitor; and (b) in presence of 2 .mu.M of Efavirentz, which is known a Non-Nucleoside Inhibitor of HIV-1 Reverse Transcriptase.

In accordance with the objects outlined above, the present invention provides methods, instruments, and kits for luminogenic (e.g., enzymatic luminescence) recognition and quantitation of nucleic acid molecules.

In various embodiments of the invention, the disclosed protocols, instruments, and kits provide improved method for producing enzymatic luminescent signal proportional to the number of copies of target molecules of interest either in the same sample substance or across plurality of sample substances and said signal is proportional to the number of copies of target molecules independently of the sequence length or molecule size of said target molecules.

In certain embodiment of this invention the disclosed protocols, instruments, and kits provide improved method for highly sensitive quantitation of the number of copies of nucleic acid molecules, which nucleic acids having the lengths less than 100-bases long.

In other embodiments, the method of present invention can be used for detection of various target molecules. Here said target molecules can form covalent or non-covalent bound with nucleic acid molecules due to mutual affinity or binding capacity, typically specific or non-specific binding interaction, including biochemical, physiological, or pharmaceutical interactions. Said biological molecules bind to nucleic acids molecule for purpose of specific recognition of the biological molecules, or equally acceptable, for labeling and detection of said biological molecules by detecting the corresponding bind nucleic acid molecules according to the method of present invention. Here nucleic acid molecules can include short and long RNA and DNA fragments, synthetic oligonucleotides, aptamers, peptide nucleic acids (PNA), oligonucleotides with incorporated analogs of deoxynucleotides, including, but not limited to, Locked Nucleic Acids, DeoxyInosine, Digoxigenin, DeoxyUridine, Methylated nucleotides, Halogenated nucleotides, Degenerated Bases (Wobbles), phosphorothioated nucleotides, and the like known to those skilled in the art.

In various embodiments of the invention determination of the number of target molecules can be performed by endpoint detection approach, in which pyrophosphate is first generated by specific replication of nucleic acid molecules of interest by polymerase or reverse transcriptase reaction at optimal temperature and buffer conditions. After completion of said replication reaction a set of enzymes and reagents is added and the number of pyrophosphate molecules is quantified by enzymatic luminescent reaction.

Yet, in some other embodiments of the present invention determination of the number of target molecules can be performed in real time by generating pyrophosphate by specific replication of nucleic acid molecules of interest by polymerase or reverse transcriptase reaction and by performing enzymatic reactions simultaneously and in the same reaction volume using an enzymatic conversion of pyrophosphate to ATP and luminescent light for detection and quantification of said pyrophosphate molecules.

In some embodiments, the above disclosed real time detection of replication of nucleic acid molecules by polymerase or reverse transcriptase can be used for measuring activity and for detection inhibition of the respective polymerase or reverse transcriptase enzyme in applications such as screening and study mechanisms of action of new polymerase and reverse transcriptase inhibitors. Indeed, at certain reaction conditions the emission rate of luminescent photons is determined by rate of pyrophosphate synthesis, which in-turn is given by activity of polymerase or respective reverse transcriptase enzyme. Reducing of polymerase activity, for instance, due to presence of an inhibitor agent in the reaction solution reduces the rate of pyrophosphate production and reduces the emission rate of luminescent photons accordingly.

Now considering end-point detection of target molecules, in various embodiments of the invention the method may comprise: (1) obtaining at least one sample substance suspected of containing one or more nucleic acids of interest, where said nucleic acids can be either RNA or DNA or fragments of thereof; (2) generating pyrophosphate by specific replication of nucleic acid molecules of interest by polymerase or reverse transcriptase at conditions when the replication reaction is self-terminating due to incorporation of terminators such as ddNTPs into the replicated sequence or due to reaching the end of the replication template; (3) once said specific replication reaction is completed and pyrophosphate molecules are accumulated in solution, enzymes and reagents are added for producing light by an enzymatic luminescence reaction, which involves the pyrophosphate molecules produced by replication reaction; (4) the number of photons produced by said enzymatic luminescence reaction is measured vs. time over a period of time, which said period of time is often longer than 1 ms and most preferably is shorter than 1 hour; (5) the kinetic parameters (e.g., shape, rate, and amplitudes of rising and decaying components of luminescent signal) are compared with that of a background luminescence from a similar reference sample kept under the condition when no replication reaction can occur due to absence of polymerase/transcriptase or due to addition of non-homologous replication template; (6) the number of target nucleic acid molecules is determined most preferably by analyzing the amplitude of the rising component of luminescent signal or from the detected number of luminescence photons.

Now considering real time detection of target molecules, in various embodiments of the invention the method may comprise: (1) obtaining at least one sample substance suspected of containing one or more nucleic acids of interest, where said nucleic acids can be either RNA or DNA or fragments of thereof; (2) generating pyrophosphate by specific replication of nucleic acid molecules of interest by polymerase or reverse transcriptase at conditions when the replication reaction is self-terminating due to incorporation of terminators such as ddNTPs into the replicated sequence or due to reaching the end of the replication template; (3) generating luminescent photons by enzymes and reagents present at the same time and in the very same reaction volume, where replication reaction is carried out and pyrophosphate molecules are produced by replication reaction; (4) measuring the emission rate of the luminescent photons vs. time or by measuring the total number of photons produced by said enzymatic luminescent reaction; (5) comparing the emission rate or the number of luminescent photons with a background luminescence from the same sample before replication reaction has been performed or from a similar reference sample under the condition when no replication reaction can occur due to absence of polymerase/transcriptase or due to addition of non-homologous replication template; (6) determining the number of target nucleic acid molecules from the detected emission rate of bioluminescence photons, or alternatively, from the total number of bioluminescent photons detected over a certain period of time.

In particular embodiments of the invention, to make the luminescent signal proportional to the number of target molecules and thus make it suitable for quantification the number of copies of target molecules, a programmable termination of polymerase or reverse transcription (RT) reaction is achieved by conducting replication reaction using a mixture of deoxynucleotides (dNTP) and dideoxynucleotides (ddNTP) as illustrated in Drawing 2. The ratio of ddNTP:dNTP defining the lengths of a cDNA transcript to be synthesized. The self-termination of the replication reaction allows generate on average the same amount of luminescent photons per each copy of target molecule for various DNA/RNA targets or DNA/RNA species, even if the corresponding target molecules have different sequence length.

Yet, in another embodiment of the invention for measurement polymerase and reverse transcriptase activity and screening polymerase inhibitors the method may comprise: (1) obtaining a sample substance containing a known quantity of primer and template nucleic acids, where said nucleic acids can be either RNA or DNA or fragments of thereof; (2) generating pyrophosphate by specific replication of nucleic acid molecules by polymerase or reverse transcriptase in presence of inhibitor of interest; (3) generating luminescent photons by enzymes and reagents present at the same time and in the very same reaction volume, where replication reaction is carried out and pyrophosphate molecules are produced by replication reaction; (4) measuring the emission rate of the luminescent photons or by measuring the total number of photons produced by said enzymatic luminescent reaction; (5) comparing the emission rate or the number of luminescent photons with a background luminescence from the same sample before replication reaction has been performed or from a similar reference sample under the condition when no replication reaction can occur due to absence of polymerase/transcriptase or due to addition of non-homologous replication template; (6) determining the activity of polymerase or respective transcriptase from the detected rate of generating bioluminescence photons.

In various embodiments of the invention, the set of enzymes and reagents for detection pyrophosphate is formulated to allow measurement of the three components of the luminescence: the pyrophosphate component (PPi), the ATP component, and steady-state background component of the luminescent signal as illustrated in Drawing 3. This is achieved by formulating a multi-enzyme assay, which produces luminescent kinetic with easily distinguishable fast rising and slow decaying components. The rising component is due to conversion of pyrophosphate to ATP and the decaying component is driven by two enzymatic reactions: one involves the consumption ATP by luciferase and the other is given by hydrolysis of pyrophosphate (PPi) to inorganic phosphate (Pi) by inorganic pyrophosphatase (PPase). The key element of this approach is the use of time-resolved measurements (i.e., kinetic assay) instead of measurements of the steady-state luminescence intensity employed, for instance, by a regenerative cycle assay known in the art. The approach of the present invention allows accurately quantify PPi in sample in presence of ATP contamination and steady-state background luminescence, which are often observed in real biological samples.

Yet, in another embodiments of the invention, the detection of short RNA such as microRNA and small DNA fragments, usually having the length of 100 bases or less, can be performed (1) by hybridizing the short target molecule RNA or DNA to a somewhat larger probe oligonucleotide molecule carrying a sequence fragment homologous to the target molecule to be detected; (2) performing polymerase extension reaction to extend the hybridized short target molecule to the full length of the probe molecule, during said extension reaction one PPi molecule is released per each incorporated deoxynucleotide; (3) producing light by a enzymatic luminescence reaction, which involves the PPi molecules produced by replication reaction; (4) measuring the rate of phoron emission or the number of photons produced by said enzymatic luminescence reaction over a period of time, which said period of time is often longer than 1 ms and most preferably is shorter than 1 hour; (5) comparing the emission rate or the total number of photons over a certain period of time with a background luminescence from the same sample before replication reaction has been performed or from a similar reference sample under the condition when no replication reaction is expected due to absence of polymerase/transcriptase or due to the use of non-homologous primer(s); (6) determining the number of target nucleic acid molecules from the detected emission rate or the number of luminescent photons.

In various embodiments, the enzymatic luminescence detection of pyrophosphate can be carried out by converting PPi into ATP by ATP-Sulfurylase followed by luciferin/luciferase bioluminescence reaction (Ronagi M., Genome Res., 11(1):2-11 (2001)), or equally acceptable, by known in the art chemiluminescence reactions for determining hydrogen peroxide as the measure of pyrophosphate in the sample (Janson V., Janson K., Anal. Biochem., 304:135-137 (2002), Nishinaka ete al, Bioche. Biophys. Res. Commun., 193:554-559 (1993)), the contents each of which are incorporated herein by reference.

Now considering bioluminescence reaction for PPi measurement, the reaction most preferably is performed according to a set of consecutive enzymatic reactions illustrated in Drawing 4.

Here the bioluminescence reaction is carried out using D-luciferin as substrate. A various known analogous of luciferase from various sources can be used, including, but not limited to, luciferase produced by bacteria, cell cultures, insects (*Photinus pyralis*, Jamaican click beetle and *Pyroplorus plagiophilamus*), marine organisms, and plants. Known from the art, pluralities of genetically engineered host cell cultures and organisms are available for producing and harvesting luciferase with the improved emission efficiency and thermal stability. A various luciferases available in market (Promega, Wis.; Sigma, Ohio; Pierce, Ill.) and can be used in accordance with the method of present invention.

In some embodiments of this invention, to avoid conversion of PPi into ATP, the bioluminescence reaction can be carried out using luciferase, which first was inhibited by L-luciferin. The release of PPi by DNA polymerase or RNA reverse transcription reaction causes isomerization of L-luciferin bound to luciferase, and this triggers bioluminescence, which intensity is proportional to the number of released PPi molecules.

Yet, in another embodiment, conversion of PPi to ATP can be carried out by pyrivate orthophosphate phosphotransferase (EC 2.7.9.1) followed by luciferin/luciferase ATP detection as illustrated in Drawing 5.

Here, the embodiments illustrated in Drawing 5 provides alternative approach for ATP production in special cases, when the use of ATP-sulfurylase has to be avoided, for instance, due to suboptimal reaction condition or presence of specific ATPase inhibitors in sample substance. A number of alternative enzymatic reactions can be used with the method of present invention for conversion pyrophosphate to ATP including, but not limited to:

(1) EC 2.4.2.17, (2) EC 2.5.1.6, (3) EC 2.7.7.1, (4) EC 2.7.7.2,
(5) EC 2.7.7.3, (6) EC 2.7.7.4, (7) EC 2.7.7.18, (8) EC 2.7.7.27,
(9) EC 2.7.7.58, (10) EC 4.6.1.1, (11) EC 6.2.1.1, (12) EC 6.2.1.3,
(13) EC 6.2.1.12, (14) EC 6.2.1.17, (15) EC 6.2.1.26, (16) EC 6.2.1.30,
(17) EC 6.3.1.1, (18) EC 6.3.1.2, (19) EC 6.3.1.5, (20) EC 6.3.2.1,
(21) EC 6.3.4.1, (22) EC 6.3.4.5, (23) EC 6.3.5.1, (24) EC 6.3.5.2, (25) EC 6.3.5.4.

Now, considering chemiluminescence detection of PPi molecules, the reaction most preferably is performed according to set of consecutive enzymatic reactions illustrated in Drawing 6.

According to the method of the present invention the bioluminescence, or equally acceptable, chemiluminescence from sample can be detected and quantified by any of known light sensitive instruments, and most preferably by luminometers available from various vendors (Berthold Detection Systems, Pforzheim Germany; Turner Design, Sunnyvale, Calif.). The instruments for luminescence detection can be equipped by various light sensitive sensors for quantitation light, said sensors include, but not limited to photomultiplier tubes, photodiodes, avalanche-type photodiodes, photoresistors, bolometers, and other types of photosensitive devices known to those skilled in the art.

For simultaneous detecting light from multiple luminescence sources or from luminescence reaction carried on a surface the suitable instrument can be equipped with integrated optical array sensor such CCD or optical CMOS array sensor, often said sensor operating at the temperature below room temperature for achieving higher detection sensitivity. Whenever possible, an instrument operating in photon-counting mode is the most preferable, although instrument operating in analog measurement mode is also can be adequate for many. Instruments for practicing the method of the present invention may be controlled by a computer and can be equipped with injectors for dispensing programmable amount of reagents into wells or tube where the replication of target molecules and enzymatic luminescence reactions are performed. The corresponding instruments can be designed to perform detection in a single tube or, equally acceptable, in multiple wells on a microtiter plate. In case of microtiter plate, the instrument can perform steps of programmable dispensing of multiple reagents into the wells of the plate according to a time schedule as required for optimal reaction conditions, maintaining desirable reaction temperature, and acquiring luminescence signal from corresponding wells of the microtiter plate maintaining a time delay and acquiring a luminescence signal over a time intervals defined by a user.

The present invention also comprises kits for use in methods of invention which can include one or more of the following components: (1) a specific primer or set of primers which hybridize to nucleic acid(s) of interest; (2) a polymerase or reverse transcriptase; (3) detection enzyme means for identifying PPi release; (4) deoxynucleotides dCTP, dGTP, dTTP and dATP.alpha.S (e.g., 2'-Deoxy-adenosine-5' (α-thio)-triphosphate) analogue which is capable of acting as substrate for a polymerase or transcriptase, but incapable of acting as a substrate for enzymatic luminescence reaction; also can be included ddCTP, ddGTP, ddTTP, and ddATP (or ddATP.alpha.S, e.g., 2'-Dideoxyadenosine-5'(α-thio)-triphosphate, a known substitution for ddATP); or they analogs capable to terminate replication reaction when corresponding ddNTP is incorporated into cDNA sequence; said deoxynucleotides can be provided each separately or as a ready to use mixture of dNTPs and ddNTPs; (5) enzymatic reagents for removing endogenous PPi from sample substance; (6) ultrafiltration devices/columns for separating endogenous PPi and ATP from target molecules of interest; (7) buffers and solutions for reconstitution the reagents from the kit and for optimizing and carrying replication and PPi detection reaction at optimal pH and ionic conditions.

The various embodiments of the method of the present invention aimed to provide fast and highly sensitive identification and measurements of nucleic acids in various life science and biomedical applications. The various disclosed approaches allow DNA and RNA quantification in a broad dynamic range; can be used for detection of DNA, as well as long (mRNA) and short (microRNA) RNA targets; the provided method requires less reagents per reaction than other techniques known in the art; normally is performed at a constant temperature and is amendable to various replication strategies including "constant temperature" PCR and rolling circle amplification; the method of present invention can be implemented using equipment, which costs a fraction of the real time RT-qPCR system.

The method of this invention has higher sensitivity and dynamic range than procedures that use microarrays, and therefore it can be used for validation of microarray results as currently performed by RT-qPCR.

The method of present invention addresses certain drawbacks of real time quantitative polymerase chain reaction (RT-qPCR) method:
 by having better accuracy due to linear scale measurement by method of this invention vs. the logarithmic scale measurement by RT-qPCR;
 by shorter assay time since no temperature cycling is required by method of this invention;
 by using less expensive reagents and equipment since only one transcriptase and only one primer per reaction are required vs. a typical RT-qPCR reaction which requires transcriptase, DNA Polymerase, RT primer and two PCR primers;
 by providing open platforms for different RNA and DNA replication strategies, including the polymerase chain reaction (PCR), ligase chain reaction (LCR), self-sustained sequence replication (3SR), nucleic acid sequence based amplification (NASBA), strand displacement amplification (SDA), amplification with Qβ replicase (Birkenmeyer and Mushahwar, J. Virological Methods, 35: 117-126 (1991); Landegren, Trends Genetics, 9: 199-202 (1993)) as well as "constant temperature" PCR and rolling circle amplification (Fire A., Xu S. Q, PNAS 92:4641-4645 (1995), incorporated herein by reference).

The method of present invention can be implemented in various commercial assays for life science research, clinical diagnosis, drug discovery, environmental analysis and other applications required identification and quantification of nucleic acids and various biological agents that can be represented by nucleic acid markers or nucleic acid precursors.

Materials and Methods.

Taq DNA Polymerase, AMV Reverse Transcriptase and dNTPs were purchased from Promega (Madison, Wis.); M-MuIV reverse transcriptase was purchased from Fermentas (Cat. No. EP0351); HIV-1 Reverse Transcriptase was purchase from Ambion (Cat. No. AM2045, Applied Biosystems/Ambion); ddNTPs and inorganic pyrophosphatase (PPAse) were purchased from USB (Cleveland, Ohio), ATP detection kit, ATP-Sulfurylase (EC2.7.7.4) and RNA-free water were purchased from Sigma-Aldrich (St. Louis, Mo.), 2'-deoxyadenosine-5'(α-thio)-triphosphate (dATP.alpha.S) was purchased from TriLink Biotechnologies (Cat. No. 8001-1, Trilink Biotechnologies, San Diego, Calif.), primer oligonucleotides were ordered from Integrated DNA Technologies (Coralville, Iowa). All other chemicals were commercially available biology-grade. Microcon centrifugal filter tubes YM100, YM10, and YM3 were purchased from Millipore (Billerica, Mass.). All solutions were freshly prepared and used immediately; luciferin-luciferase solution for ATP detection was kept on ice before adding it into the reaction solution. Luminescence measurements were conducted using Sirius tube luminometer and Orion II microplate luminometer operating in photon-counting mode (Berthold Detection Systems, Pforzheim, Germany).

EXAMPLE 1

Time-Resolved Assay for Pyrophosphate Quantitation in ATP Contaminated Samples

In this invention a principle of design and practice are disclosed for a high-sensitivity PPi assay, which allows, in a single experiment, measurement of the three components of the luminescence: the PPi component, the ATP component, and the steady-state background luminescence. This is achieved by formulating a multi-enzyme assay, which produces luminescence kinetic with easily distinguishable fast-rising and slow-decaying components. The rising kinetic component is due to conversion of PPi to ATP, and the decaying component is driven by two enzymatic reactions: one involves the consumption of ATP by luciferase and the other the hydrolysis of PPi to inorganic phosphate (Pi) by inorganic pyrophosphatase (PPase). The use of PPase allows assessment of the intensity of steady-state luminescence in biological samples for increasing sensitivity and accuracy of PPi measurements. The method of present invention has important advantage over methods known in the art specifically by providing sensitive and accurate quantitation of inorganic pyrophosphate in presence of ATP contamination and background luminescence due to non-specific substrates present in biological samples.

The method of present invention is primarily taught for nucleic acids quantitation, including quantitation of DNA, RNA and microRNA. It is appreciated that the pyrophosphate quantitation assay disclosed hereinbelow also can be used in others applications, including but not limited to, detection of pyrophosphate and ATP in various biological samples. One example, provided by way of illustration and not bay way of limitation is detection of PPi and ATP in body fluids and breath condensate from patients for diagnosis of various medical conditions.

According to the method of present invention aimed at detection pyrophosphate in ATP contaminated samples, three linked enzymatic reactions determine the kinetics of luminescence: (1) the reaction of conversion of PPi to ATP by ATP-sulfurylase; (2) the reaction of consumption of PPi by inorganic pyrophosphatase; and (3) the reaction of consumption of ATP by luciferin-luciferase, that results in photon emission, as illustrated in Drawing 4.

Pyrophosphate Detection Solution:

In various embodiments of the method of present invention provided herein by way of illustration, the assay solution for pyrophosphate detection was prepared by adding 400 femtomole of APS (Sigma, Cat. No. A5508); 100 mU of ATP-sulfurylase (Sigma, Cat. No. A8957) and 10 mU of PPase (USB, Cat. No. 70953Y) per each 40 ul ATP-detection solution (Sigma, Cat. No. FLAA). When said assay solution is added to a sample containing pyrophosphate, the solution produces luminescence having a kinetic with easily distinguishable fast-rising and slow-decaying kinetic components. The rising kinetics component is due to conversion of PPi to ATP, and the slow decay component is driven by two enzymatic reactions: one involves the consumption of ATP by luciferase and the other is due to the hydrolysis of PPi to inorganic phosphate (Pi) by inorganic pyrophosphatase (PPase). The use of PPase allows assessment of the intensity of steady-state luminescence in biological samples for increasing sensitivity and accuracy of PPi measurements.

Three requirements determine the selection respective reagents concentration of the PPi assay according to method of present invention: (1) requirement for high detection sensitivity, which, to large extent, is determined by a ratio of concentration of ATP-sulfurylase and PPase; (2) requirement for sufficient time to complete the assay, which determines the desirable time of the rising and decaying components of the luminescence kinetic; (3) requirement of dynamic range, which is driven by the concentration of APS in assay solution. In this illustrative embodiment the objective is to adjust the PPi assay reagents for optimal performance with a photon counting luminometer (Sirius and Orion models, Berthold Detection Systems, GmbH, Pforzheim, Germany). The Sirius single-tube luminometer acquires data at the rate of 5 measurements per second, and when used with a luciferin-luciferase mixture having the reaction rate of ATP consumption of $0.0120\ s^{-1}$ (Sigma, Cat. No. FL-AA, diluted: 2 according to the manufacturer protocol) it is able to detect less than 10 fg or about 20 attomole of ATP molecules. Considering 1-5 minutes as a desirable time to complete the PPi assay, the required rates of the assay reactions can be set to have the rising time of the kinetic component to be 20 sec and the decay time of 100 sec. Because the reaction rate is determined both by number of enzyme molecules in solution and by biological activity of the respective enzyme, and also taking into consideration that enzyme's activity is varied from batch to batch and from manufacturer to manufacturer, the optimal selection of enzymes concentration is performed by measuring the time of the rising and declining kinetic's components detected from a sample with known amount of pyrophosphate rather then by adding a specified amount of enzyme molecules.

Once again, by providing by way of illustration and not by way of limitation, pyrophosphate assay was prepared by adding 400 femtomole of APS (Sigma, Cat. No. A5508); 100 mU of ATP-sulfurylase (Sigma, Cat. No. A8957) and 10 mU of PPase (USB, Cat. No. 70953Y) per each 40 .mu.l ATP-detection solution (Sigma, Cat. No. FLAA) It is appreciated that the exact concentrations provided herein is for illustration purpose only. The exact concentrations can be adjusted by one skilled in the art to achieve desirable time for rising and decaying fronts of luminescent kinetic according to specific requirement of application and detection instrument used for practicing the method of present invention.

When optimizing concentration of reagents for specific application one skilled in the art will recognize that the increasing of concentration of luciferin-luciferase and ATP-sulfurylase is reducing the rise time of the luminescence kinetic. Also, increasing the concentration of pyrophosphatase is reducing the time of the decay component of luminescent kinetics.

At the desirable kinetic time of 20 s/100 s in the exemplary embodiment the luminometer acquires 500 measurement points over 100 s of the assay time. Subsequently, the amplitudes of the rising, declining and steady-state component of luminescent kinetic is measured from experimental data as illustrated in Drawing 3 and Drawing 7 for ATP-contaminated samples and different amount of pyrophosphate in sample substance. The measured luminescent kinetic vs. time is approximated by analytical expression given by:

$$I(t)=A^*\exp(-t/t.\text{sub}.1)-B^*(-t/t.\text{sub}.2)+C \quad (1)$$

herein A is amplitude of the rising component of the luminescent kinetic; B is the amplitude of declining component; C is steady-state luminescent component; $t.\text{sub}.1$ and $t.\text{sub}.2$ are time of rising and decaying of the luminescent signal. The three parameters A, B, and C from Eq. (1) representing three components of luminescent signal: the components due to presence of pyrophosphate, ATP and steady-state luminescence caused by presence of non-specific substrates in a sample substance respectively. The parameters A, B, and C can be found from the measured luminescent kinetic by data analysis algorithms such as linear and non-linear regression algorithms known in the art and provided with various software products available in market (for instance, Excel from Microsoft; SigmaPlot and TableCurve2D from Systat (Chicago, Ill.); etc.). The amount of pyrophosphate in sample is proportional to the amplitude of A; whereas the amount of ATP is given by difference of parameters A and B: (A−B).

EXAMPLE 2

Detection of DNA Replication

DNA synthesis reaction by polymerase was performed using a single stranded M13mp18 phage DNA (Sigma, Cat. No. D-8410) and −40 forward primer 5'-gttttcccagtcaggacgt-tgta-3' (SEQ ID NO: 1 from the Sequence Listing section of disclosure, incorporated herein by reference). The reaction solution was prepared by addition of 5.0 µl of 10×PCR buffer, 5 µl of 25 mM $MgCl_2$, 5 µl each of 2 mM dGTP, dCTP, dTTP, 5 µl of 2 mM dATPαS (e.g., 2'-Deoxy-adenosine-5'(α-thio)-triphosphate), 5 µl of ATP-sulfurylase, 1.5 µl of 50 µmol/µl of primer, 1 µl of the M13 template, and 20 µl of Pyrophosphate Detection Solution as disclosed herein above in illustrative Example 1. To reduce the background luminescence the dATP has been substituted with dATPαS (e.g., 2'-Deoxyadenosine-5'(α-thio)-triphosphate). Before addition to the reaction solution the M13 DNA was annealed at 95° C. for 1 min and placed on ice for 3 min. The reaction solution with no Taq Polymerase added was placed in the luminometer and background luminescence was measured. Next, 1 μl of 1.25 U/μl of Taq Polymerase was injected into the solution and luminescence signal vs. time was recorded as illustrated in Drawing 8. The measurements have been repeated with four different samples carrying different amount of M13 DNA template: $6.6 \times 10^{-21}$ mole, $6.6 \times 10^{-20}$ mole, $6.6 \times 10^{-19}$ mole, and $6.6 \times 10^{-18}$ mole as shown in Drawing 9. Here the detection sensitivity is defined as the amount of target molecules producing luminescent signal three times above the noise level of the background luminescence, which is approximately 200 RLU/s in this experiment. Accordingly, the detection sensitivity achieved in this example is estimated to be 180 of M13 mp 18 phage DNA molecules.

EXAMPLE 3

Programmable Termination of Reverse-Transcription Reaction

It is appreciated that a number of factors may affect the accuracy of measurement DNA and RNA targets in sample substance by enzymatic luminescence assays. These factors may include variation of the lengths of synthesized cDNAs due to the length distribution of DNA and mRNA target molecules, as well as interruptions of the replication reaction by DNA and RNA secondary structures. In some cases at optimized conditions, for instance, using high fidelity PCR Enzyme Mix (e.g., Epicentre's MonsterScript transcriptase in combination with addition of Betaine) a synthesis of cDNA exceeding 15 kb can be achieved (Epicentre Biotechnology, MonsterScript Reverse Transcription Kit, Cat. No. MS040910). Yet, in many applications the size of cDNA is limited to less than 3,000 bases and, the longer cDNA molecule is synthesized, the more the synthesis reaction is influenced by difficult-to-control factors.

To have an analytical quality bioluminescence signal produced by the replication reaction, it may be desirable to stop synthesis after the cDNA has reached a certain length, for instance, 300 bases. Synthesis of relatively short cDNA is more robust and can be accomplished at somewhat suboptimal replication conditions. The programmable termination of the replication synthesis can be achieved by introducing dideoxynucleotides (ddNTPs) into the replication reaction solution. Indeed, ddNTPs do not have 3' hydroxyl group, and when incorporated into cDNA sequence, ddNTPs efficiently terminate further deoxynucleotides incorporation (Sanger et al, Proc. Natl. Acad. Sci., 74(12):5463-7, 1977, incorporated herein by reference). Although here the ddNTPs are incorporated into cDNA sequence randomly and produce various length cDNA copies of the same DNA or mRNA specie, the average length of the synthesized cDNAs is accurately defined by ddNTP:dNTP ratio.

Programmable termination of a PCR reaction in this example is demonstrated by detecting M13mp18 DNA replication in reaction solutions containing ddNTP:dNTP at the ratio of 1:20, 1:50, 1:100, 1:300 and 1:1000. The 50-base long primer has been designed to hybridize to the DNA template starting at 920 base position from the DNA 3'-termini. The primer extension by PCR span through the remaining sequence of the M13mp18 DNA, thus producing DNA replicates of up to 6279 bases long, if replication reaction is not terminated.

In this example DNA synthesis has been completed first and then the amount of pyrophosphate in sample solution was measured (e.g., end-point detection). A PCR mixture of ddNTPs:dNTPs, DNA template and primer in PCR buffer (Cat. No. M7660, Promega, USA) was prepared but with no DNA polymerase added yet. The reaction solution was divided into two 25 .mu.l aliquots. Next, a 1.25 U of Taq DNA polymerase was added to one PCR aliquot while the other was kept free of polymerase (i.e., a negative control). Both reaction solutions were incubated at 40° C. for 15 min. The solutions were cooled to room temperature and 20 .mu.l of Pyrophosphate Detection Solution as described herein above in Example 1 was added to each sample before putting the sample into a Sirius luminometer (Berthold Detection Systems, Pfortheim, Germany). After measurement the luminescent signal from each sample, a difference of two signals across Taq Polymerase positive and Taq Polymerase negative samples has been calculated. Since no DNA replication is expected in the sample without Taq polymerase, the difference of two luminescent signals is proportional to the amount of PPi released by PCR reaction. The measurements have been repeated for various ratios of ddNTPs:dNTPs and the results are plotted and presented in Drawing 10. The increase of ddNTP:dNTP ratio in PCR solution produces the decrease of bioluminescence signal, which can be attributed to the decrease in the length of DNA replicates due to PCR termination after incorporation of ddNTP. In data shown in Drawing 10 a plateau of luminescent signal was observed at lower ddNTP:dTP ratios, which may indicate an interruption of PCR reaction when proceeding a long (>1,000) DNA transcript due to possible suboptimal PCR conditions.

EXAMPLE 4

RNA Quantification in a Complex RNA Mixture

In some embodiments of the method of present invention quantitation of mRNA in a total RNA sample can be performed without mRNA enrichment. Here, a reverse transcription of 6 selected genes has been detected in a sample of total RNA from baker's yeast. Microarray expression data from public databases were used to select a panel of 6 genes with high (RPS21B, ACT1), medium (ROX3, NTG1) and low (CAD1, PIO2) abundance levels. The RNA was extracted from yeast in log growth phase. Total RNA was extracted using MasterPure RNA extraction kit following the manufacturer's protocol (Cat. No. MPY80010, Epicenter Technologies, USA). Extracted RNA was subsequently cleaned up by removing the low mass fragments (<300 nt) using YM100 Microcone columns (Millipore, USA). The amount of RNA in sample solution was measured from UV absorption at 260 nm. The RNA integrity was evaluated by the ratio of 26 s:18 s bands of RNA on 1% agarose gel. Two RNA aliquots were used for preparing positive and negative control sample for reverse transcription by gene specific primer.

The reverse transcription solution (positive control) was prepared by adding 5.0 .mu.l of 10×PCR Buffer (Cat. No. M7660, Promega, USA), 5 .mu.l of 25 mM MgCl.sub.2 solution, 5 .mu.l each of 2 mM dGTP, dCTP, dTTP, 5 .mu.l of 2 mM dATP.alpha.S, 50 pmol of the corresponding gene specific primer, 30 U of AMV Reverse Transcriptase (Cat. No. M5101, Promega, USA) and 0.1 .mu.g of total RNA. The negative control sample has all the same solution constituents except AMV reverse transcriptase. No cDNA synthesis was expected in the negative control reaction solution because of the absence of reverse transcriptase. The positive and negative control solutions were incubated at 37° C. for 60 min and, after cooling to room temperature, 20 .mu.l of Pyrophosphate Detection Solution were added as described in Example 1. The difference in luminescence signal was measured across positive and transcriptase-negative control samples. The reverse transcription reaction and measurement of luminescence signal have been repeated for each of six primers specific to the panel of six selected genes.

The intensity of respective luminescence signal was plotted vs. the expression value of the corresponding gene measured using Affymetrix yeast array (Domrachev et al, Nucl. Acids Res., 30(1):207-10, 2002). For comparison of the signals from the two different platforms the ACT1 was used as the housekeeping gene for normalization of the signals detected by enzymatic luminescence and yeast microarray. Expression values of all six genes detected by method of present invention show qualitative consistency with the expression values captured by microarray experiment, as illustrated in Drawing 11.

EXAMPLE 5

Quantitation of microRNA Targets

In one embodiment of the method of present invention for detection microRNA in sample substance, probe sequence for microRNA detection includes two segments. The 3'-prime 22-base long segment is homologous to the target miRNA. The remaining segment of the probe is 48-bases long alien sequence with no homology to miRNA or mRNA in sample. For instance, for detection of human MIR-16, which is known as a housekeeping RNA, the probe with the following sequence can be used: 3'-atcgtcgtgc atttataacc gcaggagagg gagagagaga gagaggggag agagagagag agaggagagg gagagagaga gagaggggag-5' (SEQ ID NO: 2 from the Sequence Listing, incorporated herein by reference). The underlined segment has homology to the MIR-16. The 48-base tail is an alien sequence, which can be replicated in low-noise high specificity PCR mix containing only dCTP and dTTP.

Here, a low luminescence noise is achieved due to excluding dATP from this replication reaction solution. The dATP is known to be a substrate for luciferin/luciferase enzyme system and often is the dominant source of background luminescence. Also, the presence of only two types of dNTPs eliminates extension of non-specific or random primer-template duplexes, for instance microRNA:genomic DNA, which may be present in the sample substance.

It is appreciated that specificity of microRNA probe can be further enhanced by adding sequence for making a stem-loop at the probe 3'-end or by covalently attaching a non-nucleotide chemical group at 3'-end for selecting against microRNA precursor, as known in the art (Chen et al, Nucl. Acids Res., 33(20)e179, 2005, herein incorporated by reference).

The reaction conditions for replication and detection of microRNA can be used as describe herein above: the extracted microRNA first is cleaned up by removing the low mass fragments (<10 nt, YM3 Microcone columns, Millipore, USA). The amount of RNA in sample solution is measured by UV absorption at 260 nm. The overall RNA integrity can be evaluated by measuring the ratio of 26 s:18 s bands of total RNA on 1% agarose gel or by BioAnalyzer (Applied Biosystems, USA). Two RNA aliquots need be prepared for using as positive and negative control samples for reverse transcription by gene specific primer. In this example, the reverse transcription solution (positive control) has been prepared in total 20 .mu.l of reaction solution by adding 2.0 .mu.l of 10× reaction buffer (Cat. No. KL04011K, Epicentre Biotechnology, USA), 1 .mu.l each of 10 mM dGTP, dCTP, dTTP, 1 .mu.l of 10 mM dATP.alpha.S, 50 pmol of the corresponding microRNA specific primer, 25U Exo-Minus Kienow DNA polymerase (Cat. No. KL04011K, Epicentre Biotechnology, USA) and 0.1 .mu.g of total RNA. The negative control sample can carry all the same reaction solution except Klenow DNA polymerase or can be prepared using a nonhomologous primer. No cDNA synthesis is expected in the negative control sample because of the absence of polymerase or homologous primer. The positive and negative control samples incubated at 37° C.-42° C. for 30 min and, after cooling to room temperature, 20 .mu.l of Pyrophosphate Detection Solution as described herein above in Example 1 is added. The luminescent signal from each positive and negative control sample is measured and difference of bioluminescence signal across two sample is calculated, which said difference quantitatively represents the amount of target microRNA in sample substance.

EXAMPLE 6

Luminescent Polymerase Activity Assay

In some embodiments, the method of present invention can be used for measurement activity of reverse transcriptase (or equally acceptable DNA polymerase) in presence or absence of a reverse transcriptase inhibitor in applications, such as, but not limited to, discovery of new antiviral drugs.

Two of the four main classes of licensed antiviral drugs are Nucleoside and Non-Nucleoside Reverse Transcriptase Inhibitors (e.g., NRTI and NNRTI respectively). These two classes of drugs are particularly important for treatment of HIV-1 infection The Reverse Transcriptase Inhibitors selectively inhibit HIV-1 reverse transcriptase and disrupt integration of viral genome to the host DNA, thus preventing virus from replication. Discovery of new NRTI and NNRTI requires screening a large number of compounds for inhibition of activity of reverse transcriptase of interest (e.g., HIV-1 in this example). Currently screening is performed mostly using radioactive-labeling method, which is time consuming and present health safety concern for workers (Zhang et al, Antimicrob. Agents and Chemotherapy, 50(8) 2772-2781, (2006), incorporated herein by reference).

In method of present invention, assessment of the activity of HIV-1 reverse transcriptase inhibitor was performed by detecting in real time the release of pyrophosphate by reverse transcription reaction in presence of inhibitor of interest. HIV-1 reverse transcriptase was purchased from Ambion (Cat. No. AM2045, Applied Biosystems/Ambion, USA). A 3'-poly(A) microbial RNA and specific primer were purchased from Fermentas (Cat. No. K1611, Fermentas, USA). Reaction solution was prepared in 20 .mu.l volume by adding 0.1 .mu.g of bacterial 3'-poly(A) RNA; 20 pmol of sequence-specific primer; 4 .mu.l of 5× buffer (Cat. No. AM2045, Applied Biosystems/Ambion, USA); 1 .mu.l each of 10 mM dCTP, dGTP, dTTP; 1 .mu.l of 10 mM dATP.alpha.S; 20U of RiboLock ribonuclease inhibitor (Cat. No. K1611, Fermentas) and 20 .mu.l of pyrophosphate detection solution as disclosed herein above in Example 1. Two or more identical aliquots of the reaction solution have been used to prepare a positive sample (e.g., HIV-1 transcriptase added); a negative control sample (e.g., no HIV-1 transcriptase added); and samples with HIV-1 transcriptase and different amount of NNRTI inhibitor added (Efavirentz, Cat. No. E425000, Toronto Research Chemicals, Canada). Samples as described herein above were placed in wells of 96-well microplate and HIV-1 transcriptase and certain amount of inhibitor (Efavirentz), were added to respective wells. Luminescence from each well vs. time was measured using Orion II microplate luminometer operating in photon-counting mode (Berthold Detection System, Pfortzheim, Germany). Luminescence from well with no added HIV-1 transcriptase was used to establish luminescence base line, which was subsequently subtracted from luminescence data from wells, to which HIV-1 transcriptase and inhibitor (if any) were added. Increasing amount of inhibitor in the sample reduces the activity of HIV-1 transcriptase and causes a drop of intensity of luminescence as illustrated by plot in Drawing 12. By measuring the intensity of luminescence at certain moment of time and plotting it vs. the amount of inhibitor added to the corresponding sample a half maximal effective concentration (EC50) can be determined, at which activity of transcriptase is 50% of the activity of non-inhibited transcriptase. The E50 value is commonly used as a measure of drug potency and is important criteria for selection new drug compound and optimizing drug performance.

EXAMPLE 7

Chemiluminescence Method for Nucleic Acids Quantitation

Yet, in some embodiments of the method of present invention enzymatic chemiluminescence detection can be used for quantitation of number of copies of nucleic acid in a sample substance. Various modification of the method can be introduce by employing chemiluminescence detection of inorganic pyrophosphate released by self-terminating nucleic acid replication reaction as disclosed hereinabove.

In one embodiment, inorganic pyrophosphate is hydrolyzed by pyrophosphatase (E.C. 3.6.1.1) to inorganic phosphate, which is reacted with inosine in presence of purine nucleoside phosphorylase (E.C. 2.4.2.1) to produce hypoxanthine, which forms uric acid in the presence of xanthine oxidase (E.C. 1.1.3.22), and may be measured either by the absorbance of the uric acid, or by the formazan formed when a tetrazolium salt is used as the oxidant.

Also can be used approach in which inorganic phosphate is determined by reacting with xanthosine in the presence of purine nucleoside phosphorylase (E.C. 2.4.2.1) and xanthine oxidase (E.C. 1.1.3.22) to produce hydrogen peroxide, which is reacted with a chromogenic peroxidase substrate in the presence of peroxidase.

Yet, in another approach, inorganic phosphate is determined by reacting it with inosine in the presence of purine nucleoside phosphorylase (E.C. 2.4.2.1), xanthine oxidase (E.C. 1.1.3.22) and uricase to produce hydrogen peroxide, which is reacted with luminol in the presence of the heme portion of cytochrome c (microperoxidase) to produce chemiluminescence.

Also can be used assay for inorganic pyrophosphate which comprises: a) reacting inorganic pyrophosphate present in a sample with inosine 5'-monophosphate or xanthosine 5'-monophosphate in the presence of hypoxanthine phosphoribosyltransferase (E.C. 2.4.2.8) or xanthine phosphoribosyltransferase (E.C. 2.4.2.22), xanthine oxidase (E.C. 1.1.3.22), $Mg^{2+}$ ion or another divalent cation, a buffering agent, and optionally uricase; and b) determining production of hydrogen peroxide as a measure of inorganic pyrophosphate in the sample.

In some applications, determining production of hydrogen peroxide may comprise reacting the hydrogen peroxide with a chemoluminescent peroxidase substrate, such as luminol, in the presence of peroxidase (E.C. 1.11.1.7), and measuring chemiluminescence as a measure of production of hydrogen peroxide, and thereby as a measure of inorganic pyrophosphate in the sample.

Chemiluminescence Nucleic Acid Quantitation.

In one embodiment of the method of present invention, a stock solution for chemoluminescent detection of PPi released by replication reaction can be prepared in a volume of 1 ml by addition of 1000 .mu.M IMP (inosine 5'-monophosphate), sodium salt (Sigma 14500); 150 units of hypoxanthine phosphoribosyl transferase (EC 2.4.2.8), from bakers yeast (Sigma H3389); 0.2 U of xanthine oxidase (EC 1.1.3.22), from buttermilk (Fluka 95493); 0.2 U of uricase (EC 1.7.3.3), from *Arthrobacter globiformis* (Sigma U7128); 5.2 U of peroxidase (EC 1.11.1.7), from horseradish (Sigma P8375); 50 .mu.M luminol (5-amino-2,3-dihydro-1,4-phthalazinedione), sodium salt (Sigma A4685); 10 mM $MgCl_2$ (Sigma M1028); and 200 mM Tris-HCl buffer at pH 8.3 (Sigma T5128).

An approximately equal amount of the chemiluminescence detection solution and the replication reaction solution are mixed and luminescence intensity of the mixture is measured. Here, to have luminescence signal proportional to the number of target molecules regardless of the length of target molecules, the target nucleic acid is replicated by self-terminating reaction solution in presence of ddNTP:dNTP mixture, as disclosed herein above in Example 3. Alternatively, for detection of microRNA, the replication reaction can be carried out using a primer, which is longer than the target microRNA. The primer is hybridized to the target microRNA and the PCR extension reaction is performed, which elongates the microRNA to the full length of the hybridized primer, as disclosed herein above in Example 5. The chemiluminescence signal subsequently is quantified by measuring light emitted from the mixture prepared by addition of the chemiluminescence detection solution and the replication solution. For accurate determination of the pyrophosphate molecules that have been released by replication, a background luminescence is recorded from a negative control sample, in which the replication reaction has been subdued due to the absence of polymerase/transcriptase or due to the use of non-homologous primer. Here, the intensity of the luminescence signal is the measure of the number of copies of nucleic acid molecules in the sample substance.

EXAMPLE 7

Rolling Circle Amplification for Quantitative Immunoassay

The use of DNA amplification for the detection of Antibodies (Abs) bound to Antigenes (Ags) has been documented previously (Schweitzer et al, PNAS USA 97:1013-1019 (2000), incorporated herein by reference), which herein incorporated by reference. In immuno-PCR, a unique DNA sequence tag is associated with a specific antibody using streptavidin-biotin interactions, alternative bridging moieties, or covalent linkage. Abs bound to Ag are then detected by PCR amplification of the associated DNA tag. Multiple Abs and multiple DNA tags have been used (Hacia J., Nature Genet., 21:4247 (1999), incorporated herein by reference) to analyze several Ags simultaneously. Although immuno-PCR was shown to be significantly more sensitive than ELISA, gel electrophoresis was required after DNA amplification in solution to separate and/or quantitate the different amplified DNA tags. The requirements for thermal cycling and product separation by gel electrophoresis have restricted the widespread adoption of immuno-PCR as an alternative to ELISA and have precluded its utility in immunohistochemical or array formats.

RCA driven by DNA polymerase can replicate circularized oligonucleotide probes with either linear or geometric kinetics under isothermal conditions (Lizardi et al, Nature Genet., 19:225-232 (1998), incorporated herein by reference). Using a single primer, RCA generates hundreds of tandemly linked copies of the circular template within a few minutes. In ImmunoRCA, the 5' end of this primer is attached to an Ab. In the presence of circular DNA, DNA polymerase, and nucleotides, the rolling circle reaction results in a DNA molecule consisting of multiple copies of the circle DNA sequence that remains attached to the Ab. The amplified DNA can be detected by detecting released inorganic pyrophosphate according to the method of the present invention, herein providing means for quantifying the number rolling circle replication events. ImmunoRCA, therefore, represents a novel approach for signal amplification of Ab-Ag recognition events. It is appreciated that RCA reactions can be carried out with either linear or geometric kinetics (Schweitzer et al, PNAS USA 97:1013-1019 (2000), incorporated herein by reference in its entirety) in presence of ddNTPs for programmable termination of RCA reaction. Here, the construction of AB-DNA conjugates is described and the utility of using these conjugates to detect Ags in several different immunoRCA formats is demonstrated.

The sequences used for immunoRCA detection of prostate-specific Ag (PSA) and avidin can be as follows: conjugate primer 1,5'-thiol-aaaaaa aaaaaa aaacac agc tga gcatag gacat-3' (SEQ ID NO: 3); circle 1,5'-ctcagc tgtgta acaaca tgaaga ttgtag gtcaga actcac ctgtta gaaact gtgaag atcgct tattat gtccta tc-3' (SEQ ID NO: 4); detectors, 5'-aacaac atg aag attgta-3' (SEQ ID NO: 5), 5'-tcagaa ctcacc tgttag-3' (SEQ ID NO: 6), 5'-actgtg aagatc gcttat-3' (SEQ ID NO: 7); (ii) for IgE and sheep IgG: conjugate primer 2,5'-thiol-gtacca tcatat atgtcc gtgcta gaagga aacagt tac A-3' (SEQ ID NO: 8); circle 2,5'-tag cacgga catata tgatgg taccgc agtatg agtatc tcctat cactac taagtg gaagaa atgtaa ctgttt cct tc-3' (SEQ ID NO: 9); detectors, 5'-tatatg atggta ccgcag-3' (SEQ ID NO: 10), 5'-tgagta tctcct atgact-3' (SEQ ID NO: 11), 5'-taagtg gaa gaa atgtaa-3' (SEQ ID NO: 12), where all respective sequences are listed in the Sequence Listing section of the disclosure and incorporated herein by reference.

In carrying out the methods of the present invention, said circular DNA may be derived from a padlock probe and a portion of a target sequence is derived from a padlock gap-fill in procedure. [See: Nilsson et al, "Padlock Probes: Circularizing Oligonucleotides for Localized DNA Detection", Science, 265: 2085-2088 (1994), Lizardi, U.S. Pat. No. 5,854, 033, incorporated herein by reference] As before, these embodiments of the present invention may further comprise detecting the pyrophosphate release as replication, including replication by Rolling Circle Amplification, is proceeded.

RCA reaction. Circle 1 DNA (200 nM) in 10 μl φ29 buffer [250 mM Tris.HCl (pH 7.5); 50 mM MgCl$_2$; 1 mg/ml BSA] was added to the sample substance and incubated at 45° C. for 30 min. Ten microliters of RCA reaction mixture (2 mM dATP.alpha.S; 2 mM dCTP; 2 mM dGTP; 1.5 mM dTTP; 2 .mu.M ddATP.alpha.S; 2 .mu.M ddCTP; 2 .mu.M ddGTP; 1.5 .mu.M ddTTP; 0.5 mM FITC-dUTP; .phi.29 buffer; 0.4 units; .mu.l .phi.29 polymerase) can be added to the sample substance and incubated at 37° C. for 30 min. It is appreciated that the amount of ddATP, ddTTP, ddGTP, and ddCTP can be reduced to achieve the longer target replication cycle and, accordingly, the higher detection sensitivity as may be required in specific applications of the method of present invention.

EXAMPLE 8

Detection of Target Molecules in High-Throughput Format

In some embodiments, this invention provides means for quantitation of gene expression in high throughput 96- and 384-well format. The assay can be performed on a microplate luminometer equipped with two injectors (for instance, Orion II microplate luminometer, Berthold Detection Systems, Pforzheim, Germany). The present invention addresses two issues for implementing high-throughput nucleic acid quantitation: (1) maximizing assay sensitivity to compensate a lower detection sensitivity of microplate luminometer vs. the sensitivity of a single tube device; (2) optimizing assay time to perform quick analysis on 96- and 384-well plates.

The focus of the assay optimization is on achieving a short, <1 min, burst of bioluminescence signal associated with all PPi molecules accumulated from replication reaction over an extended, e.g., approximately 15 min period of time. Indeed, by increasing concentration of reagents of pyrophosphate detection solution conditions can be achieved for generating light by a short, for instance 30 sec or shorter light burst. The shorter luminescence time can be achieved by completing replication reaction and pyrophosphate to ATP conversion, thus maximizing ATP content before adding ATP-Detection Solution. Also, the concentration of luciferin/luciferase in detection solution can be increased to achieve higher ATP to light reaction rate. Here, shortening the luminescence burst increasing luminescence intensity and reducing time required to complete measurements for a large number of wells, that can be processed consequtively or in parallel.

When performing measurements using microplate luminometer, on each plate some number of samples/wells normally is reserved for negative controls to measure background luminescence from reaction solution in absence of transcriptase or by addition of alien sequence primer. The average background luminescence of the negative control wells is averaged and subtracted accordingly from the luminescence signal detected from wells carrying samples, in which content of target nucleic acid molecules need be measured.

The invention claimed is:

1. A method of quantitation of inorganic pyrophosphate in a sample, comprising: a) obtaining at least one sample suspected of containing inorganic pyrophosphate molecules; b) adding pyrophosphate detection solution to said sample, wherein said pyrophosphate detection solution utilizes ATP sulfurylase, 5'-phosphosulphate (APS), luciferin-luciferase and inorganic pyrophosphatase (PPase); c) detecting intensity of luminescent light vs, time from said sample with said pyrophosphate detection solution added; d) measuring amplitudes of the rising and decaying components of said luminescent intensity vs. time; e) calculating the amount of inorganic pyrophosphate and ATP present in said sample, wherein the amount of pyrophosphate is proportional to the rising component of luminescent intensity vs. time and the amount of ATP is proportional to the difference between the rising and decaying component of the luminescent signal.

2. The method of claim 1, wherein inorganic pyrophosphate is generated by a nucleic acid replication reaction.

3. The method of claim 2, wherein the nucleic acid replication reaction is carried out in presence of dideoxynucleotides.

4. The method of claim 1, wherein inorganic pyrophosphate is generated by a nucleic acid replication reaction and wherein said reaction is carried out in presence of an inhibitor of the nucleic acid replication reaction.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Unknown
<220> FEATURE:
<223> OTHER INFORMATION: M13 phage DNA -40 primer -continued

```
<400> SEQUENCE: 1
gttttcccag tcaggacgtt gta                                              23

<210> SEQ ID NO 2
<211> LENGTH: 90
<212> TYPE: DNA
<213> ORGANISM: Unknown
<220> FEATURE:
<223> OTHER INFORMATION: Probe for detection human MIR-16 microRNA

<400> SEQUENCE: 2
atcgtcgtgc atttataacc gcaggagagg gagagagaga gagaggggag agagagagag      60
agaggagagg gagagagaga gagaggggag                                       90

<210> SEQ ID NO 3
<211> LENGTH: 35
<212> TYPE: DNA
<213> ORGANISM: Unknown
<220> FEATURE:
<223> OTHER INFORMATION: Conjugate primer for detection prostate-
      specific antigen

<400> SEQUENCE: 3
aaaaaaaaaa aaaaacacag ctgaggatag gacat                                 35

<210> SEQ ID NO 4
<211> LENGTH: 80
<212> TYPE: DNA
<213> ORGANISM: Unknown
<220> FEATURE:
<223> OTHER INFORMATION: Circle 1 probe for immunoRCA assay

<400> SEQUENCE: 4
ctcagctgtg taacaacatg aagattgtag gtcagaactc acctgttaga aactgtgaag      60
atcgcttatt atgtcctatc                                                  80

<210> SEQ ID NO 5
<211> LENGTH: 18
<212> TYPE: DNA
<213> ORGANISM: Unknown
<220> FEATURE:
<223> OTHER INFORMATION: Detector 1 of 6 for immunoRCA

<400> SEQUENCE: 5
aacaacatga agattgta                                                    18

<210> SEQ ID NO 6
<211> LENGTH: 18
<212> TYPE: DNA
<213> ORGANISM: Unknown
<220> FEATURE:
<223> OTHER INFORMATION: Detector 2 of 6 for immunoRCA

<400> SEQUENCE: 6
tcagaactca cctgttag                                                    18

<210> SEQ ID NO 7
<211> LENGTH: 18
<212> TYPE: DNA
<213> ORGANISM: Unknown
<220> FEATURE:
<223> OTHER INFORMATION: Detector 3 of 6 for immunoRCA

<400> SEQUENCE: 7
actgtgaaga tcgcttat                                                    18
```

```
<210> SEQ ID NO 8
<211> LENGTH: 40
<212> TYPE: DNA
<213> ORGANISM: Unknown
<220> FEATURE:
<223> OTHER INFORMATION: Conjugate primer 2 for RCA

<400> SEQUENCE: 8
gtaccatcat atatgtccgt gctagaagga aacagttaca                              40

<210> SEQ ID NO 9
<211> LENGTH: 80
<212> TYPE: DNA
<213> ORGANISM: Unknown
<220> FEATURE:
<223> OTHER INFORMATION: Circle 2 for immunoRCA

<400> SEQUENCE: 9
tagcacggac atatatgatg gtaccgcagt atgagtatct cctatcacta ctaagtggaa        60
gaaatgtaac tgtttccttc                                                    80

<210> SEQ ID NO 10
<211> LENGTH: 18
<212> TYPE: DNA
<213> ORGANISM: Unknown
<220> FEATURE:
<223> OTHER INFORMATION: Detector 4 of 6 for immunoRCA

<400> SEQUENCE: 10
tatatgatgg taccgcag                                                      18

<210> SEQ ID NO 11
<211> LENGTH: 20
<212> TYPE: DNA
<213> ORGANISM: Unknown
<220> FEATURE:
<223> OTHER INFORMATION: Detector 5 of 6 fro immunoRCA

<400> SEQUENCE: 11
tgagtatctc ctatgactcy                                                    20

<210> SEQ ID NO 12
<211> LENGTH: 20
<212> TYPE: DNA
<213> ORGANISM: Unknown
<220> FEATURE:
<223> OTHER INFORMATION: Detector 6 of 6 for immunoRCA

<400> SEQUENCE: 12
cytaagtgga agaaatgtaa                                                    20
```